(12) United States Patent
Uvnäs-Moberg et al.

(10) Patent No.: US 9,034,821 B2
(45) Date of Patent: May 19, 2015

(54) PHARMACEUTICAL COMPOSITION

(76) Inventors: Kerstin Uvnäs-Moberg, Växjö (SE);
Anders Carlsson, Växjö (SE)

( * ) Notice: Subject to any disclaimer, the term of this patent is extended or adjusted under 35 U.S.C. 154(b) by 0 days.

(21) Appl. No.: 14/111,072

(22) PCT Filed: Apr. 13, 2012

(86) PCT No.: PCT/EP2012/056813
§ 371 (c)(1),
(2), (4) Date: Dec. 13, 2013

(87) PCT Pub. No.: WO2012/140216
PCT Pub. Date: Oct. 18, 2012

(65) Prior Publication Data
US 2014/0171369 A1    Jun. 19, 2014

Related U.S. Application Data

(60) Provisional application No. 61/475,471, filed on Apr. 14, 2011.

(30) Foreign Application Priority Data

Apr. 14, 2011   (SE) ...................................... 1150324

(51) Int. Cl.
*A61K 38/11*  (2006.01)
*A61P 5/10*  (2006.01)
*A61K 47/38*  (2006.01)
*A61K 38/08*  (2006.01)

(52) U.S. Cl.
CPC ................ *A61K 47/38* (2013.01); *A61K 38/11* (2013.01); *A61K 38/08* (2013.01)

(58) Field of Classification Search
CPC .............................. A61K 38/08; A61K 47/38
See application file for complete search history.

(56) References Cited

U.S. PATENT DOCUMENTS

| 5,763,405 | A | * | 6/1998 | Fjellestad-Paulsen et al. | ................ 514/10.9 |
| 5,833,647 | A | * | 11/1998 | Edwards | ......................... 604/22 |
| 7,727,959 | B2 | * | 6/2010 | Uvnas-Moberg et al. | ... 514/11.6 |
| 7,884,076 | B2 | * | 2/2011 | Welch | ........................... 514/11.6 |
| 2007/0032410 | A1 | * | 2/2007 | Quay et al. | ......................... 514/9 |

FOREIGN PATENT DOCUMENTS

| EP | 0943326 A1 | 9/1999 | |
| EP | 2248518 A1 | 11/2010 | |
| WO | WO0178758 | * 10/2001 | ............. A61K 38/11 |
| WO | WO 2008/042452 A1 | 4/2008 | |
| WO | WO 2010/118888 A1 | 10/2010 | |

OTHER PUBLICATIONS

Definition: 'Unit of Oxytoxcin' accessed online at http://www.medilexicon.com/medicaldictionary.php?t=95735 on May 31, 2014. 1 page.*
Wang et al. Characterization of a female controlled drug delivery system for microbicides. Contraception, 2002. vol. 66, pp. 281-287.*
Carlsson, A., "Nonionic Cellulose Ethers: Interactions with Surfactants, Solubility and Other Aspects," Doctoral Dissertation, Sep. 29, 1989, Lund University, Sweden, pp. 1-7.
Handbook of Pharmaceutical Excipients, Sixth Edition, Edited by Rowe, Raymond C., Sheskey, Paul J., and Quinn, Marian E., Pharmaceutical Press, London, UK, pp. 326-329.
Karlstrom, G., et al., "Phase Diagrams of Nonionic Polymer-Water Systems. Experimental and Theoretical Studies of the Effects of Surfactants and Other Cosolutes," J. Phys. Chem. 1990;94:5005-5015.

* cited by examiner

*Primary Examiner* — Marcela M Cordero Garcia
(74) *Attorney, Agent, or Firm* — Cermak Nakajima & McGowan LLP; Malcolm K. McGowan

(57) ABSTRACT

The present invention relates to a novel pharmaceutical composition comprising oxytocin and/or one or more fragment(s) and/or variant(s) thereof and at least one non-ionic cellulose ether, such as hydroxypropylmethylcellulose, said pharmaceutical composition having a low pH. The present pharmaceutical composition has been shown to provide an exceptionally suitable environment for oxytocin, as the stability thereof has increased significantly as compared to previous compositions with this molecule. The pharmaceutical composition according to the invention can be used for medical purposes, such as in the treatment of climacteric disorders.

32 Claims, No Drawings

SEQUENCE LISTING

```
<160> NUMBER OF SEQ ID NOS: 24

<210> SEQ ID NO 1
<211> LENGTH: 9
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: AMIDATION

<400> SEQUENCE: 1

Cys Tyr Ile Gln Asn Cys Pro Leu Gly
1               5

<210> SEQ ID NO 2
<211> LENGTH: 10
<212> TYPE: PRT
<213> ORGANISM: Artificial sequence
<220> FEATURE:
<223> OTHER INFORMATION: Human oxytocin fragments and variants
<220> FEATURE:
<221> NAME/KEY: MISC_FEATURE
<222> LOCATION: (1)..(1)
<223> OTHER INFORMATION: X1 can be Cys or nothing
<220> FEATURE:
<221> NAME/KEY: MISC_FEATURE
<222> LOCATION: (2)..(2)
<223> OTHER INFORMATION: X2 can be Tyr, Phe or nothing
<220> FEATURE:
<221> NAME/KEY: MISC_FEATURE
<222> LOCATION: (3)..(3)
<223> OTHER INFORMATION: X3 can be Ile, Val, Homophenylalanine, Phe,
<223> OTHER INFORMATION: Cyclohexylalanine or nothing
<220> FEATURE:
<221> NAME/KEY: MISC_FEATURE
<222> LOCATION: (4)..(4)
<223> OTHER INFORMATION: X4 can be Gln, Ser, Thr, Citrulline, Arg or
      Diaminobutyric acid
<220> FEATURE:
<221> NAME/KEY: MISC_FEATURE
<222> LOCATION: (7)..(7)
<223> OTHER INFORMATION: X5 (position 7) can be Pro or nothing
<220> FEATURE:
<221> NAME/KEY: MISC_FEATURE
<222> LOCATION: (8)..(8)
<223> OTHER INFORMATION: X6 (position 8) can be Ile, Leu, nothing, Val,
      Homoserine,
<223> OTHER INFORMATION: Diaminobutyric acid, Thr, Arg or Citrulline
<220> FEATURE:
<221> NAME/KEY: MISC_FEATURE
<222> LOCATION: (9)..(9)
<223> OTHER INFORMATION: X7 (position 9) can be Gly, nothing or Ala
<220> FEATURE:
<221> NAME/KEY: MOD_RES
<222> LOCATION: (10)..(10)
<223> OTHER INFORMATION: AMIDATION
<220> FEATURE:
<221> NAME/KEY: MISC_FEATURE
<222> LOCATION: (10)..(10)
<223> OTHER INFORMATION: X8 (position 10) can be Gly or nothing
```

<400> SEQUENCE: 2

Xaa Xaa Xaa Xaa Asn Cys Xaa Xaa Xaa Xaa
1               5                   10

<210> SEQ ID NO 3
<211> LENGTH: 9
<212> TYPE: PRT
<213> ORGANISM: Artificial sequence
<220> FEATURE:
<223> OTHER INFORMATION: Mesotocin, found in birds
<220> FEATURE:
<221> NAME/KEY: MOD_RES
<222> LOCATION: (9)..(9)
<223> OTHER INFORMATION: AMIDATION

<400> SEQUENCE: 3

Cys Tyr Ile Gln Asn Cys Pro Ile Gly
1               5

<210> SEQ ID NO 4
<211> LENGTH: 9
<212> TYPE: PRT
<213> ORGANISM: Artificial sequence
<220> FEATURE:
<223> OTHER INFORMATION: Isotocin, found in fish
<220> FEATURE:
<221> NAME/KEY: MOD_RES
<222> LOCATION: (9)..(9)
<223> OTHER INFORMATION: AMIDATION

<400> SEQUENCE: 4

Cys Tyr Ile Ser Asn Cys Pro Ile Gly
1               5

<210> SEQ ID NO 5
<211> LENGTH: 9
<212> TYPE: PRT
<213> ORGANISM: Eisenia foetida
<220> FEATURE:
<223> OTHER INFORMATION: Annetocin
<220> FEATURE:
<221> NAME/KEY: MOD_RES
<222> LOCATION: (9)..(9)
<223> OTHER INFORMATION: AMIDATION

<400> SEQUENCE: 5

Cys Phe Val Arg Asn Cys Pro Thr Gly
1               5

<210> SEQ ID NO 6
<211> LENGTH: 9
<212> TYPE: PRT
<213> ORGANISM: Artificial sequence
<220> FEATURE:
<223> OTHER INFORMATION: Vasotocin, found in non-mammalian vertebrates
      and fetal mammals
<220> FEATURE:
<221> NAME/KEY: MOD_RES
<222> LOCATION: (9)..(9)
<223> OTHER INFORMATION: AMIDATION

<400> SEQUENCE: 6

Cys Tyr Ile Gln Asn Cys Pro Arg Gly
1               5

<210> SEQ ID NO 7
<211> LENGTH: 9
<212> TYPE: PRT

```
<213> ORGANISM: Homo sapiens
<220> FEATURE:
<223> OTHER INFORMATION: Vasopressin
<220> FEATURE:
<221> NAME/KEY: MOD_RES
<222> LOCATION: (9)..(9)
<223> OTHER INFORMATION: AMIDATION

<400> SEQUENCE: 7

Cys Tyr Phe Gln Asn Cys Pro Arg Gly
1               5

<210> SEQ ID NO 8
<211> LENGTH: 6
<212> TYPE: PRT
<213> ORGANISM: Artificial sequence
<220> FEATURE:
<223> OTHER INFORMATION: Human oxytocin fragment
<220> FEATURE:
<221> NAME/KEY: MOD_RES
<222> LOCATION: (6)..(6)
<223> OTHER INFORMATION: AMIDATION

<400> SEQUENCE: 8

Cys Tyr Ile Gln Asn Cys
1               5

<210> SEQ ID NO 9
<211> LENGTH: 7
<212> TYPE: PRT
<213> ORGANISM: Artificial sequence
<220> FEATURE:
<223> OTHER INFORMATION: Human oxytocin fragment
<220> FEATURE:
<221> NAME/KEY: MOD_RES
<222> LOCATION: (7)..(7)
<223> OTHER INFORMATION: AMIDATION

<400> SEQUENCE: 9

Cys Tyr Ile Gln Asn Cys Pro
1               5

<210> SEQ ID NO 10
<211> LENGTH: 8
<212> TYPE: PRT
<213> ORGANISM: Artificial sequence
<220> FEATURE:
<223> OTHER INFORMATION: Human Oxytocin fragment
<220> FEATURE:
<221> NAME/KEY: MOD_RES
<222> LOCATION: (8)..(8)
<223> OTHER INFORMATION: AMIDATION

<400> SEQUENCE: 10

Cys Tyr Ile Gln Asn Cys Pro Leu
1               5

<210> SEQ ID NO 11
<211> LENGTH: 8
<212> TYPE: PRT
<213> ORGANISM: Artificial sequence
<220> FEATURE:
<223> OTHER INFORMATION: Human Oxytocin fragment
<220> FEATURE:
<221> NAME/KEY: MOD_RES
<222> LOCATION: (8)..(8)
<223> OTHER INFORMATION: AMIDATION

<400> SEQUENCE: 11

Tyr Ile Gln Asn Cys Pro Leu Gly
```

<210> SEQ ID NO 12
<211> LENGTH: 7
<212> TYPE: PRT
<213> ORGANISM: Artificial sequence
<220> FEATURE:
<223> OTHER INFORMATION: Human Oxytocin fragment
<220> FEATURE:
<221> NAME/KEY: MOD_RES
<222> LOCATION: (7)..(7)
<223> OTHER INFORMATION: AMIDATION

<400> SEQUENCE: 12

Ile Gln Asn Cys Pro Leu Gly
1               5

<210> SEQ ID NO 13
<211> LENGTH: 6
<212> TYPE: PRT
<213> ORGANISM: Artificial sequence
<220> FEATURE:
<223> OTHER INFORMATION: Human Oxytocin fragment
<220> FEATURE:
<221> NAME/KEY: MOD_RES
<222> LOCATION: (6)..(6)
<223> OTHER INFORMATION: AMIDATION

<400> SEQUENCE: 13

Gln Asn Cys Pro Leu Gly
1               5

<210> SEQ ID NO 14
<211> LENGTH: 5
<212> TYPE: PRT
<213> ORGANISM: Artificial sequence
<220> FEATURE:
<223> OTHER INFORMATION: Human Oxytocin fragment
<220> FEATURE:
<221> NAME/KEY: MOD_RES
<222> LOCATION: (5)..(5)
<223> OTHER INFORMATION: AMIDATION

<400> SEQUENCE: 14

Ile Gln Asn Cys Pro
1               5

<210> SEQ ID NO 15
<211> LENGTH: 10
<212> TYPE: PRT
<213> ORGANISM: Artificial sequence
<220> FEATURE:
<223> OTHER INFORMATION: Human Oxytocin variant
<220> FEATURE:
<221> NAME/KEY: MOD_RES
<222> LOCATION: (10)..(10)
<223> OTHER INFORMATION: AMIDATION

<400> SEQUENCE: 15

Cys Tyr Ile Gln Asn Cys Pro Leu Gly Gly
1               5                   10

<210> SEQ ID NO 16
<211> LENGTH: 6
<212> TYPE: PRT
<213> ORGANISM: Artificial sequence
<220> FEATURE:
<223> OTHER INFORMATION: Human Oxytocin variant
<220> FEATURE:
<221> NAME/KEY: MOD_RES

```
<222> LOCATION: (6)..(6)
<223> OTHER INFORMATION: AMIDATION

<400> SEQUENCE: 16

Gln Asn Cys Pro Leu Leu
1               5

<210> SEQ ID NO 17
<211> LENGTH: 9
<212> TYPE: PRT
<213> ORGANISM: Artificial sequence
<220> FEATURE:
<223> OTHER INFORMATION: Human Oxytocin variant
<220> FEATURE:
<221> NAME/KEY: MOD_RES
<222> LOCATION: (9)..(9)
<223> OTHER INFORMATION: AMIDATION

<400> SEQUENCE: 17

Cys Tyr Val Thr Asn Cys Pro Leu Gly
1               5

<210> SEQ ID NO 18
<211> LENGTH: 9
<212> TYPE: PRT
<213> ORGANISM: Artificial sequence
<220> FEATURE:
<223> OTHER INFORMATION: Human Oxytocin variant
<220> FEATURE:
<221> NAME/KEY: MISC_FEATURE
<222> LOCATION: (3)..(3)
<223> OTHER INFORMATION: X is Homophenylalanine
<220> FEATURE:
<221> NAME/KEY: MOD_RES
<222> LOCATION: (9)..(9)
<223> OTHER INFORMATION: AMIDATION

<400> SEQUENCE: 18

Cys Tyr Xaa Thr Asn Cys Pro Val Gly
1               5

<210> SEQ ID NO 19
<211> LENGTH: 9
<212> TYPE: PRT
<213> ORGANISM: Artificial sequence
<220> FEATURE:
<223> OTHER INFORMATION: Human Oxytocin variant
<220> FEATURE:
<221> NAME/KEY: MISC_FEATURE
<222> LOCATION: (4)..(4)
<223> OTHER INFORMATION: X is Citrulline
<220> FEATURE:
<221> NAME/KEY: MOD_RES
<222> LOCATION: (9)..(9)
<223> OTHER INFORMATION: AMIDATION

<400> SEQUENCE: 19

Cys Tyr Phe Xaa Asn Cys Pro Leu Gly
1               5

<210> SEQ ID NO 20
<211> LENGTH: 9
<212> TYPE: PRT
<213> ORGANISM: Artificial sequence
<220> FEATURE:
<223> OTHER INFORMATION: Human Oxytocin variant
<220> FEATURE:
<221> NAME/KEY: MISC_FEATURE
<222> LOCATION: (3)..(3)
<223> OTHER INFORMATION: X is Cyclohexylalanine
<220> FEATURE:
```

```
<221> NAME/KEY: MISC_FEATURE
<222> LOCATION: (8)..(8)
<223> OTHER INFORMATION: X is Homoserine
<220> FEATURE:
<221> NAME/KEY: MOD_RES
<222> LOCATION: (9)..(9)
<223> OTHER INFORMATION: AMIDATION

<400> SEQUENCE: 20

Cys Tyr Xaa Arg Asn Cys Pro Xaa Ala
1               5

<210> SEQ ID NO 21
<211> LENGTH: 9
<212> TYPE: PRT
<213> ORGANISM: Artificial sequence
<220> FEATURE:
<223> OTHER INFORMATION: Human Oxytocin variant
<220> FEATURE:
<221> NAME/KEY: MISC_FEATURE
<222> LOCATION: (4)..(4)
<223> OTHER INFORMATION: X is Diaminobutyric acid
<220> FEATURE:
<221> NAME/KEY: MISC_FEATURE
<222> LOCATION: (8)..(8)
<223> OTHER INFORMATION: X is Diaminobutyric acid
<220> FEATURE:
<221> NAME/KEY: MOD_RES
<222> LOCATION: (9)..(9)
<223> OTHER INFORMATION: AMIDATION

<400> SEQUENCE: 21

Cys Tyr Val Xaa Asn Cys Pro Xaa Ala
1               5

<210> SEQ ID NO 22
<211> LENGTH: 9
<212> TYPE: PRT
<213> ORGANISM: Artificial sequence
<220> FEATURE:
<223> OTHER INFORMATION: Human Oxytocin variant
<220> FEATURE:
<221> NAME/KEY: MISC_FEATURE
<222> LOCATION: (3)..(3)
<223> OTHER INFORMATION: X is Homophenylalanine
<220> FEATURE:
<221> NAME/KEY: MISC_FEATURE
<222> LOCATION: (4)..(4)
<223> OTHER INFORMATION: X is Diaminobutyric acid
<220> FEATURE:
<221> NAME/KEY: MISC_FEATURE
<222> LOCATION: (8)..(8)
<223> OTHER INFORMATION: X is Citrulline
<220> FEATURE:
<221> NAME/KEY: MOD_RES
<222> LOCATION: (9)..(9)
<223> OTHER INFORMATION: AMIDATION

<400> SEQUENCE: 22

Cys Tyr Xaa Xaa Asn Cys Pro Xaa Ala
1               5

<210> SEQ ID NO 23
<211> LENGTH: 9
<212> TYPE: PRT
<213> ORGANISM: Artificial sequence
<220> FEATURE:
<223> OTHER INFORMATION: Human Oxytocin variant
<220> FEATURE:
<221> NAME/KEY: MOD_RES
<222> LOCATION: (9)..(9)
<223> OTHER INFORMATION: AMIDATION
```

```
<400> SEQUENCE: 23

Cys Tyr Phe Arg Asn Cys Pro Val Ala
1               5

<210> SEQ ID NO 24
<211> LENGTH: 9
<212> TYPE: PRT
<213> ORGANISM: Artificial sequence
<220> FEATURE:
<223> OTHER INFORMATION: Human Oxytocin variant
<220> FEATURE:
<221> NAME/KEY: MISC_FEATURE
<222> LOCATION: (3)..(3)
<223> OTHER INFORMATION: X is Cyclohexylalanine
<220> FEATURE:
<221> NAME/KEY: MISC_FEATURE
<222> LOCATION: (4)..(4)
<223> OTHER INFORMATION: X is Citrulline
<220> FEATURE:
<221> NAME/KEY: MOD_RES
<222> LOCATION: (9)..(9)
<223> OTHER INFORMATION: AMIDATION

<400> SEQUENCE: 24

Cys Tyr Xaa Xaa Asn Cys Pro Arg Gly
1               5
```

PHARMACEUTICAL COMPOSITION

CROSS-REFERENCE TO RELATED APPLICATIONS

This application is a national phase of International Application PCT/EP2012/056813, filed Apr. 13, 2012, which claims the benefit of priority under 35 USC §119 to U.S. Provisional Application No. 61/475,471 filed on Apr. 14, 2011 and Swedish Application No. 1150324-0 filed Apr. 14, 2011, each of which is herein incorporated by reference in its entirety.

FIELD OF THE INVENTION

The present invention relates to pharmaceutical compositions based on non-ionic cellulose ethers, and more specifically to such pharmaceutical compositions comprising oxytocin, and/or fragments and/or variants thereof, as disclosed herein, said pharmaceutical compositions having an improved stability. Oxytocin is a natural peptide well known in the art to have various therapeutic applications, such as in the treatment of climacteric disorders and cancers, especially pre-cancerous conditions, associated therewith.

BACKGROUND

Oxytocin was one of the first peptide hormones to be isolated and sequenced. It is a nonapeptide with two cysteine residues that form a disulfide bridge between positions 1 and 6 and corresponds to the formula

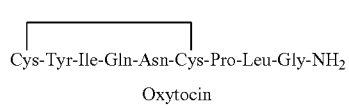

(SEQ ID NO: 1)

Oxytocin

For a long time the only effects attributed to oxytocin were its stimulating effects on milk ejection and uterine contractions, but in the past decades it has been shown that oxytocin exerts a wide spectrum of effects within the central nervous system, CNS. It has been suggested that oxytocin participates in the control of memory and learning processes and of various types of behaviour such as feeding, locomotion, as well as maternal and sexual behaviour. Oxytocin is also suggested to participate in the control of cardiovascular functions, thermoregulation, pain threshold and fluid balance, as well as in wound healing. There is also evidence that oxytocin is involved in the control of various immunological processes. It has also been demonstrated that oxytocin injections cause a lowering of blood pressure and increased weight gain with long lasting effects after repetitive administration. As a central stimulating substance oxytocin plays an important role in the interaction between mother and progeny in mammals. The products may also be used as prophylactics in young human beings e.g. already in new born babies or young children to prevent the development of diseases later on in life, which diseases are dependent on stress conditions during the fetal life. Such conditions may be heart/vessel diseases such as stroke, heart infarct, hypertension, and diabetes. In the human body oxytocin is produced in the paraventricular nucleus, PVN, and the supraoptic nucleus, SON, of the hypothalamus. It differs by only two amino acids from vasopressin, which is also produced in these nuclei. The magnocellular oxytocinergic neurones of the SON and PVN send oxons to the posterior pituitary from which oxytocin is released into the circulation. Parvocellular neurones that originate in the PVN project into multiple areas within CNS. The oxytocin-producing cells are innervated by cholinergic, catecholaminergic, seroronergic as well as peptidergic neurones. The presence of oxytocin in different tissues outside the brain, such as the uterus, ovaries, testis, thymus, adrenal medulla and pancreas has been demonstrated and oxytocin is suggested to exert local effects in these organs. A parallel secretion of oxytocin into the brain regions and into the circulation occurs in response to some stimuli such as suckling, but other stimuli can cause separate activation of oxytocinergic neurones, terminating in the brain or the pituitary.

Cellulose ethers are named after, and based on, cellulose which is a renewable material and the most common chemical compound in organic nature. There is a broad range of cellulose ethers available on the market, both ionic and non-ionic, for example sodium carboxymethylcellulose, hydroxyethylethylcellulose, hydroxyethylcellulose, hydroxypropylcellulose, hydroxyethylmethylcellulose and hydroxypropylmethycellulose.

Cellulose ethers are used as additives in such diverse applications as food, paint, oil recovery, paper, cosmetics, pharmaceuticals, adhesives, printing, agriculture, ceramics, textiles, detergents and building materials. Cellulose ethers improve the product quality in these applications and act as thickeners, water retention agents, suspending aids, protecting colloids, film formers or thermoplastics in such different products as dispersion paints, drilling muds, ice cream, tablet coatings, wallpaper paste and tile adhesive.

Non-ionic cellulose ethers such as methylcellulose, hydroxypropylmethylcellulose (also referred to as hypromellose) and methylhydroxyethylcellulose, are widely used in the pharmaceutical industry due to their ability to thicken, bind and retain water, as well as to emulsify and suspend particles and form films. Further information regarding non-ionic cellulose ethers can be found e.g. in WO92/09307.

The peptide structure of oxytocin makes it vulnerable to degradation, and it is a well-known fact that pharmaceutical compositions comprising oxytocin should be stored in a cool environment (about 4° C.) to avoid substantial degradation and/or aggregation thereby losing its biological function. For example, it is recommended that Syntocinon® (Novartis), a concentrated aqueous solution of oxytocin for injection/infusion, should normally be stored at 2-8° C. The shelf-life at 25° C. for this product is limited to 3 months. Another example is Syntocinon® nasal spray, which also should be stored at 2-8° C. These aqueous formulations comprise buffers, preservatives, acids, salt, co-solvents and other water-soluble additives but no gelling agent.

Previous formulations with oxytocin comprising the ionic gelling agent sodium carboxymethylcellulose (CMC) have been shown to not provide a suitable environment for oxytocin. This is for example illustrated in the experimental section of the present application.

Accordingly, in view of the problems associated with previous pharmaceutical compositions comprising oxytocin, there is a need in the art to overcome or at least mitigate some of the disadvantages in the art by providing pharmaceutical compositions wherein the stability of oxytocin is improved. Such pharmaceutical compositions will provide for more convenient storage, such as in room temperature, and should also retain their biological activity for a longer period of time.

SUMMARY OF THE INVENTION

The problems posed in the above have now been solved by the present invention, which is further explained herein.

Accordingly, the present invention relates to new pharmaceutical compositions comprising oxytocin, and/or one more fragment(s) and/or variant(s) thereof as disclosed herein, as well as pharmaceutically acceptable salts thereof, and at least one non-ionic cellulose ether, as disclosed herein, wherein said pharmaceutical composition has a pH within the range of between about 3 and 4.

It has surprisingly been shown that a neutral, non-ionic cellulose ether, such as hydroxypropylmethylcellulose (HPMC), significantly improves the stability of oxytocin in a pharmaceutical composition, thereby providing a pharmaceutical composition excellent for pharmaceutical use. Accordingly, the present invention relates to pharmaceutical compositions comprising oxytocin (SEQ ID NO:1), and/or one or more fragment(s) and/or variant(s) thereof according to SEQ ID NO:2, or as otherwise defined herein, as well as pharmaceutically acceptable salts thereof and at least one non-ionic cellulose ether, such as hydroxypropylmethylcellulose (HPMC).

This stabilizing effect of the non-ionic cellulose ether is further supported by said pharmaceutical composition having a low pH, such as within the range of between about 3 and 4, such as within the range of between about 3 and 3.5. This will make it possible to store oxytocin in room temperature for longer periods of time than previously possible, when present in such a pharmaceutical composition. A favourable environment for the oxytocin peptide in such a pharmaceutical composition should also positively affect its biological activity thereby improving its therapeutic effect as more biologically active substance is present therein throughout time.

Hence, the present invention relates to pharmaceutical compositions comprising oxytocin (SEQ ID NO:1), and/or one or more fragment(s) and/or variant(s) thereof according to SEQ ID NO:2, as well as pharmaceutically acceptable salts thereof and at least one non-ionic cellulose ether, such as hydroxypropylmethylcellulose (HPMC), said pharmaceutical composition having a pH within the range of between about 3 and 4, such as about 3 and 3.5, or as otherwise exemplified herein, wherein the stability of oxytocin and/or one or more fragment(s) and/or variant(s) thereof has been improved. The ability of a non-ionic cellulose ether, such as HPMC, to stabilize oxytocin is not previously known and is highly desirable, as it has been a long felt need in the art to provide pharmaceutical compositions comprising oxytocin that do not always need to be stored in a cold environment, and which are thereby easier to handle.

The present invention also relates to medical uses of a pharmaceutical composition as disclosed herein, such as in the treatment of vaginal atrophy. Hence, in other aspects the present invention also relates to the use of oxytocin, and/or one or more fragment(s) and/or variant(s) thereof and at least one non-ionic cellulose ether as disclosed herein in the manufacture of a medicament, said medicament having a pH within the range of between about 3 and 4 for the treatment of a climacteric disorder, such as vaginal atrophy. In addition, the invention relates to a method for preparing said pharmaceutical composition, as well as methods of treating a patient with a pharmaceutical composition according to the invention.

DETAILED DESCRIPTION

Definitions

Whenever "oxytocin", "oxytocin peptide" and/or "oxytocin molecule" is referred to herein, this encompasses oxytocin (SEQ ID NO:1) and/or one or more fragment(s) and/or variant(s) thereof as defined herein according to the general formula SEQ ID NO:2, or any other variant and/or fragment as mentioned herein, as well as analogues and/or homologues thereof. Whenever a fragment, variant or homologue of an oxytocin molecule/peptide is envisaged it is to be understood that such a variant, fragment or homologue encompasses a biological activity comparable to the oxytocin molecule itself (SEQ ID NO:1). As an example, it can be shown that a substance has oxytocin activity by performing tests showing the activity of the actual substance, e.g. by performing a double blind cross-over randomised protocol as described in WO0178758 (Example 1).

Accordingly, a "variant" of oxytocin as referred to herein, refers to a peptide which has been varied in its amino acid structure as compared to the oxytocin molecule in that some amino acid positions may have been altered by introducing other amino acids in such positions, such as natural or unnatural amino acids as exemplified herein, or it may have been extended by adding one or more natural or unnatural amino acid(s) to either ends of the peptide. In addition, other structural variations may also have been performed to the present peptides as referred to herein, such as synthetic modifications. Said "variant" still maintains a biological activity similar to oxytocin and said oxytocin variant is also stabilized by being present in a pharmaceutical composition according to the present invention.

Furthermore, a "fragment" of oxytocin, as referred to herein is a peptide which comprises a part of the amino acid sequence of oxytocin, but wherein one or more amino acids may have been removed from one or both of the amino acid terminal end(s). This term also refers to a fragment of a oxytocin variant as defined in SEQ ID NO:2, hence meaning that also encompassed by the present invention is any fragment of a peptide as presented by SEQ ID NO:2.

A "pH regulating agent" is any agent, such as a liquid agent, such as an aqueous liquid, which is able to regulate and/or maintain the pH of said pharmaceutical composition, wherein said pH is kept approximately in a selected range, which selected range is exemplified herein. Such a pH regulating agent can for example be a buffer, such as a citrate, lactate or phosphate buffer. A "buffer" is an ionic compound, usually a salt of a weak acid or base, added to a solution to resist changes in its acidity or alkalinity and thus stabilize its pH. A buffer solution is a solution containing such a compound. Other examples of a pH regulating agents are organic and inorganic acids and bases, such as acetic acid, citric acid, phosphoric acid, hydrochloric acid and sodium hydroxide.

Oxytocin is known to suffer from problems due to degradation and/or aggregation which make it preferable to store pharmaceutical compositions comprising oxytocin in a cool environment to avoid that it loses its biological activity. Surprisingly, it has now been shown that it is possible to prepare pharmaceutical compositions comprising oxytocin and/or one or more fragment(s) and/or variant(s) thereof, as illustrated in SEQ ID NO:1 and SEQ ID NO:2, with improved stability by utilizing at least one non-ionic cellulose ether as a pharmaceutical carrier for said oxytocin molecule, in combination with a low pH. Accordingly, the present invention relates to pharmaceutical compositions comprising oxytocin (SEQ ID NO:1), and/or one or more fragment(s) and/or variant(s) thereof according to SEQ ID NO:2, or as otherwise defined herein, as well as pharmaceutically acceptable salts thereof and at least one non-ionic cellulose ether, such as hydroxypropylmethylcellulose (HPMC).

When referring to an improved stability of said pharmaceutical composition, it is the stability of the biological substance, i.e. oxytocin and/or one or more fragment(s) and/or variant(s) thereof as defined herein that is improved. Hence thereby, the biological activity and the therapeutic effect of a pharmaceutical composition as presented herein should be improved, by avoiding too much degradation and/or aggregation, or other structural change of the oxytocin substance.

Without being bound by any specific theory, the non-ionic cellulose ether, being an uncharged molecule, appears to stabilize the oxytocin molecule by avoiding unnecessary interference therewith, i.e. with said oxytocin molecule. Furthermore, the usage of a suitable pH, such as a pH within the range of between about 3 and 4, such as within the range of between about 3 and 3.5, further contributes to the stabilizing effect on oxytocin of the non-ionic cellulose ether. Hence, again not wishing to be bound by a specific theory, the low pH appears not only to stabilize oxytocin itself, but it is also favourable for the non-ionic cellulose ether part of the composition.

In combination, this provides an excellent composition for pharmaceutical use, wherein the biological and/or therapeutic activity of oxytocin and/or a variant and/or a fragment thereof as exemplified herein should be increased and prolonged. This pharmaceutical composition is also easier to handle for the user, as due to its improved stability it need not always be stored in a cool environment, but can instead more conveniently be kept in room temperature, e.g. during use or storage, still retaining its biological activity.

The stabilizing effect of a non-ionic cellulose ether on the oxytocin molecule in a pharmaceutical composition of the present invention is in contrast to other used pharmaceutical carriers, such as for example sodium carboxymethylcellulose (CMC), in which formulation oxytocin has been shown to more rapidly degrade and/or aggregate (see for example the comparative examples in the experimental section). Without being bound by a specific theory, this could be due to the fact that the CMC polymer is negatively charged and may be regarded as a polyanion which could interact unfavourably with the oxytocin peptide.

Accordingly, the present invention relates to a pharmaceutical composition comprising
a. oxytocin (SEQ ID NO:1), and/or one or more fragment(s) and/or variant(s) thereof according to SEQ ID NO:2, as well as pharmaceutically acceptable salts thereof; and
b. at least one non-ionic cellulose ether;
wherein SEQ ID NO:2 is $X_1$—$X_2$—$X_3$—$X_4$-Asn-Cys-$X_5$—$X_6$—$X_7$—$X_8$—$NH_2$ wherein
$X_1$ is selected from the group consisting of Cys and nothing;
$X_2$ is selected from the group consisting of Tyr, Phe, and nothing;
$X_3$ is selected from the group consisting of Ile, Val, Hoph, Phe, Cha, and nothing;
$X_4$ is selected from the group consisting of Gln, Ser, Thr, Cit, Arg, and Daba;
$X_5$ is selected from the group consisting of Pro and nothing;
$X_6$ is selected from the group consisting of Ile, Leu, nothing, Val, Hos, Daba, Thr, Arg, and Cit;
$X_7$ is selected from the group consisting of Gly, nothing, and Ala;
$X_8$ is selected from the group consisting of Gly and nothing;
wherein said pharmaceutical composition has a pH within the range of between about 3 and about 4.

In one aspect on the present invention, when $X_1$ is Cys then a disulfide is formed between $X_1$ and Cys.

Accordingly, it is to be understood that when $X_1$ in formula (I) is cysteine (Cys) then the thiol group of $X_1$ may form a disulfide with the thiol group of the cystein that is located between the asparagine (Asn) and $X_5$ thereby forming a cyclic structure of formula (Ia):

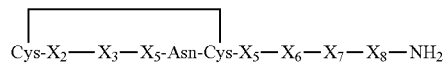

In a further aspect, there is provided a pharmaceutical composition comprising oxytocin (SEQ ID NO:1) and hydroxypropylmethylcellulose, and wherein the pH of said pharmaceutical composition is within the range of between about 3 and 4, such as between about 3 and 3.5, or as otherwise exemplified herein.

In a further aspect, the present invention also relates to a pharmaceutical composition consisting of a non-ionic cellulose ether and oxytocin (SEQ ID NO:1), and/or a variant and/or a fragment thereof as presented herein (SEQ ID NO:2), as well as pharmaceutically acceptable salts thereof, and a pH regulating agent, wherein said pharmaceutical composition has a pH within the range of between about 3 and 4, such as within the range of about 3 and about 3.5. In one aspect, said pharmaceutical composition consists of oxytocin (SEQ ID NO:1), hydroxypropylmethylcellulose (HPMC), and a pH regulating agent, wherein said pharmaceutical composition has a pH within the range of between about 3 and 4, such as between about 3 and about 3.5, or as otherwise exemplified herein. In one aspect, said pH regulating agent is a buffer, such as a citrate or a lactate buffer.

In one aspect of the present invention, said pharmaceutical composition comprises oxytocin, i.e. when $X_1$ is Cys, $X_2$ is Tyr, $X_3$ is Ile, $X_4$ is Gln, $X_5$ is Pro, $X_6$ is Leu, $X_7$ is Gly, and $X_8$ is nothing in SEQ ID NO:2, (Cys-Tyr-Ile-Gln-Asn-Cys-Pro-Leu-Gly-$NH_2$) (SEQ ID NO:1).

The one or more variant(s) and/or fragment(s) of oxytocin of said pharmaceutical composition (SEQ ID NO:2) can also be selected from the group consisting of the following compounds, as well as pharmaceutically acceptable salts thereof:

```
                                                    (SEQ ID NO: 3)
Mesotocin: Cys-Tyr-Ile-Gln-Asn-Cys-Pro-Ile-Gly-NH2
X1 is Cys, X2 is Tyr, X3 is Ile, X4 is Gln, X5 is
Pro, X6 is Ile, X7 is Gly, and X8 is nothing;

(SEQ ID NO: 4)
Isotocin: Cys-Tyr-Ile-Ser-Asn-Cys-Pro-Ile-Gly-NH2
X1 is Cys, X2 is Tyr, X3 is Ile, X4 is Ser, X5 is
Pro, X6 is Ile, X7 is Gly, and X8 is nothing;

(SEQ ID NO: 5)
Annetocin: Cys-Phe-Val-Arg-Asn-Cys-Pro-Thr-Gly-NH2
X1 is Cys, X2 is Phe, X3 is Val, X4 is Arg, X5 is
Pro, X6 is Thr, X7 is Gly, and X8 is nothing;

(SEQ ID NO: 6)
Vasotocin: Cys-Tyr-Ile-Gln-Asn-Cys-Pro-Arg-Gly-NH2
X1 is Cys, X2 is Tyr, X3 is Ile, X4 is Gln, X5 is
Pro, X6 is Arg, X7 is Gly, and X8 is nothing;

(SEQ ID NO: 7)
Vasopressin: Cys-Tyr-Phe-Gln-Asn-Cys-Pro-Arg-Gly-
NH2
X1 is Cys, X2 is Tyr, X3 is Phe, X4 is Gln, X5 is
Pro, X6 is Arg, X7 is Gly, and X8 is nothing;
```

(SEQ ID NO: 8)
Cys-Tyr-Ile-Gln-Asn-Cys-NH$_2$
X$_1$ is Cys, X$_2$ is Tyr, X$_3$ is Ile, X$_4$ is Gln, and
X$_5$-X$_8$ is nothing;

(SEQ ID NO: 9)
Cys-Tyr-Ile-Gln-Asn-Cys-Pro-NH$_2$
X$_1$ is Cys, X$_2$ is Tyr, X$_3$ is Ile, X$_4$ is Gln, X$_5$ is
Pro, and X$_6$-X$_8$ is nothing;

(SEQ ID NO: 10)
Cys-Tyr-Ile-Gln-Asn-Cys-Pro-Leu-NH$_2$
X$_1$ is Cys, X$_2$ is Tyr, X$_3$ is Ile, X$_4$ is Gln, X$_5$ is
Pro, X$_6$ is Leu, and X$_{7-8}$ is nothing;

(SEQ ID NO: 11)
Tyr-Ile-Gln-Asn-Cys-Pro-Leu-Gly-NH$_2$
X$_1$ is nothing, X$_2$ is Tyr, X$_3$ is Ile, X$_4$ is Gln,
X$_5$ is Pro, X$_6$ is Leu, X$_7$ is Gly, and X$_8$ is nothing;

(SEQ ID NO: 12)
Ile-Gln-Asn-Cys-Pro-Leu-Gly-NH$_2$
X$_1$-X$_2$ is nothing, X$_3$ is Ile, X$_4$ is Gln, X$_5$ is
Pro, X$_6$ is Leu, X$_7$ is Gly, and X$_8$ is nothing;

(SEQ ID NO: 13)
Gln-Asn-Cys-Pro-Leu-Gly-NH$_2$
X$_1$-X$_3$ is nothing, X$_4$ is Gln, X$_5$ is Pro, X$_6$ is
Leu, X$_7$ is Gly, and X$_8$ is nothing;

(SEQ ID NO: 14)
Ile-Gln-Asn-Cys-Pro-NH$_2$
X$_1$-X$_2$ is nothing, X$_3$ is Ile, X$_4$ is Gln, X$_5$ is
Pro, and X$_6$-X$_8$ is nothing;

(SEQ ID NO: 15)
Cys-Tyr-Ile-Gln-Asn-Cys-Pro-Leu-Gly-Gly-NH$_2$
X$_1$ is Cys, X$_2$ is Tyr, X$_3$ is Ile, X$_4$ is Gln, X$_5$ is
Pro, X$_6$ is Leu, X$_7$ is Gly, and X$_8$ is Gly;

(SEQ ID NO: 16)
Gln-Asn-Cys-Pro-Leu-Leu-NH$_2$
X$_1$-X$_3$ is nothing, X$_4$ is Gln, X$_5$ is Pro, X$_6$ is
Leu, X$_7$ is Leu, and X$_8$ is nothing;

(SEQ ID NO: 17)
Cys-Tyr-Val-Thr-Asn-Cys-Pro-Leu-Gly-NH$_2$
X$_1$ is Cys, X$_2$ is Tyr, X$_3$ is Val, X$_4$ is Thr, X$_5$ is
Pro, X$_6$ is Leu, X$_7$ is Gly, and X$_8$ is nothing;

(SEQ ID NO: 18)
Cys-Tyr-Hoph-Thr-Asn-Cys-Pro-Val-Gly-NH$_2$
X$_1$ is Cys, X$_2$ is Tyr, X$_3$ is Hoph, X$_4$ is Thr, X$_5$
is Pro, X$_6$ is Val, X$_7$ is Gly, X$_8$ is nothing;

(SEQ ID NO: 19)
Cys-Tyr-Phe-Cit-Asn-Cys-Pro-Leu-Gly-NH$_2$
X$_1$ is Cys, X$_2$ is Tyr, X$_3$ is Phe, X$_4$ is Cit, X$_5$ is
Pro, X$_6$ is Leu, X$_7$ is Gly, and X$_8$ is nothing;

(SEQ ID NO: 20)
Cys-Tyr-Cha-Arg-Asn-Cys-Pro-Hos-Ala-NH$_2$
X$_1$ is Cys, X$_2$ is Tyr, X$_3$ is Cha, X$_4$ is Arg, X$_5$ is
Pro, X$_6$ is Hos, X$_7$ is Ala, and X$_8$ is nothing;

(SEQ ID NO: 21)
Cys-Tyr-Val-Daba-Asn-Cys-Pro-Daba-Ala-NH$_2$
X$_1$ is Cys, X$_2$ is Tyr, X$_3$ is Val, X$_4$ is Daba, X$_5$
is Pro, X$_6$ is Cit, X$_7$ is Ala, and X$_8$ is nothing;

(SEQ ID NO: 22)
Cys-Tyr-Hoph-Daba-Asn-Cys-Pro-Cit-Ala-NH$_2$
X$_1$ is Cys, X$_2$ is Tyr, X$_3$ is Hoph, X$_4$ is Daba, X$_5$
is Pro, X$_6$ is Cit, X$_7$ is Ala, and X$_8$ is nothing;

(SEQ ID NO: 23)
Cys-Tyr-Phe-Arg-Asn-Cys-Pro-Val-Ala-NH$_2$
X$_1$ is Cys, X$_2$ is Tyr, X$_3$ is Phe, X$_4$ is Arg, X$_5$ is
Pro, X$_6$ is Val, X$_7$ is Ala, and X$_8$ is nothing;
and (SEQ ID NO: 24)
Cys-Tyr-Cha-Cit-Asn-Cys-Pro-Arg-Gly-NH$_2$
X$_1$ is Cys, X$_2$ is Tyr, X$_3$ is Cha, X$_4$ is Cit, X$_5$ is
Pro, X$_6$ is Arg, X$_7$ is Gly, X$_8$ is nothing;

Accordingly, in one aspect, the present invention relates to a pharmaceutical composition, wherein said one or more fragment(s) and/or variant(s) of oxytocin is/are selected from the group consisting of the peptides corresponding to SEQ ID NO:3-SEQ ID NO:24.

The unnatural amino acids in said substances have the following structures:

Cyclohexylalanine, herein referred to as Cha,

Homophenylalanine, herein referred to as Hoph,

Citrulline, herein referred to as Cit,

Diaminobutyric acid, herein referred to as Daba, and

Homoserine, herein referred to as Hos,

When a position in SEQ ID NO:2 is stated as being "nothing" it means that it represents a single bond between the items (letter, atom or group).

Other variants of oxytocin could also be used in the pharmaceutical compositions according to the present invention, such as naturally occurring or artificially modified variants, analogues, and/or derivatives of oxytocin, mesotocin, isotocin, and/or annetocin. Such variants could be obtained by addition, insertion, elimination, or substitution of at least one amino acid in these hormones. Other substances include precursors, metabolites such as metabolic derivatives e.g. metabolic degradation products, agonists, or analogues of the substances mentioned herein displaying the same properties.

Metabolic derivatives or metabolic degradation products may be oxytocin like peptides, e.g. with nine amino acids such as oxytocin, mesotocin, isotocin, and annetocin from which one or more amino acids has been deleted from either the carboxyl terminal end or the amino terminal end or both the carboxyl terminal and the amino terminal end, such as 1-3 amino acids from each terminal. In certain aspects, one, two or three amino acids may have been deleted from the carboxy terminal end i.e. Gly only, Gly and Leu, or Gly, Leu, and Pro. Preferably one, two or three amino may have been deleted from the amino terminal i.e. Cys only, Cys and Tyr, or Cys, Tyr, and Ile.

In certain aspects one, two or three amino acids may have been deleted both from carboxy terminal end i.e. Gly only, Gly and Leu, or Gly, Leu, and Pro, and one, two or three amino acids may have been deleted from the amino end i.e. Cys only, Cys and Tyr, or Cys, Tyr, and Ile. It could be ascertained that these variants are analogues of oxytocin, mesotocin, isotocin or annetocin by immunological methods, e.g. RIA (radioimmunoassay), IRMA (radiometric methods), RIST (radioimmunosorbent test), and RAST (radioallergosorbent test). The invention also includes variants of oxytocin having at least 50, 60, 70, 80, 90, 95, 96, 97, 98, or 99% sequence identity to oxytocin, said variants showing an oxytocin activity, as defined herein.

Annetocin has been isolated from the earthworm, as described in Oumi T. Ukena K, Matsushima O, Ikeda T, Fujita T, Minakata H, Nomoto K, Annetocin: an oxytocin-related peptide isolated from the earthworm, *Eisenia foetida*, Biochem Biophys Res Commun 1994, Jan. 14; 198(1); 393-399.

There is also a possibility to create new compounds with oxytocin activity by means of computer simulation. Methods for computer simulation are known by a person skilled in the art, e.g. as described in EP 0660 210 A2.

The invention also relates to a pharmaceutical composition comprising oxytocin or a variant thereof in both D- and L-form, as well as racemates thereof. In certain aspects the invention relates to the L-form. By inversion of the peptide sequence thereof, the D-form could be converted to the L-form. These and the peptides above can be produced by methods known to a person skilled in the art, e.g. according to Merrifield, P. B., "Solid Phase Synthesis", Angew. Chemie, 1985, No. 97, p. 801.

The pharmaceutical compositions according to the invention may in certain circumstances contain substances that extend or strengthen the effects of oxytocin. Such substances could increase the release of oxytocin and/or the member or affinity of oxytocin receptors, such as oestrogen, or drugs having an [alpha]$_2$-agonistic effect, such as clonidine.

It should be noted that pharmaceutically acceptable salts of the compounds according to the invention are included within the scope of the invention. Examples of salts of the compounds are pharmaceutically acceptable acid and base addition salts.

The expression "pharmaceutically acceptable acid addition salts" are intended to be any non-toxic organic or inorganic acid addition salt of the compounds of SEQ ID NO: 1 or SEQ ID NO: 2, and/or any other variants and/or fragments of oxytocin as described herein. Examples of illustrative inorganic acids that form suitable salts are hydrochloric acid, hydrobromic acid, sulphuric acid, phosphoric acid and acid metal salts such as sodium monohydrogen ortophosphate and potassium hydrogensulphate. Examples of illustrative organic acids that form suitable salts are mono-, di- and tricarboxylic acids. Examples of such acids are acetic acid, glycolic acid, lactic acid, pyruvic acid, malonic acid, succinic acid, glutaric acid, fumaric acid, malic acid, tartaric acid, citric acid, ascorbic acid, maleic acid, hydroxymaleic acid, benzoic acid, hydroxybenzoic acid, phenylacetic acid, cinnamic acid, salicylic acid, 2-phenoxybenzoic acid, and sulphonic acids such as p-toluenesulphonic acid, metha-nesulphonic acid and 2-hydroxyethanesulphonic acid. Such salts could either be in hydrated or anhydrous form. The acid addition salts of these compounds are generally water soluble and different hydrophilic organic solvents and, that compared to the free base forms thereof, generally display higher melting points.

The expression "pharmaceutically acceptable base addition salts" are intended to be any non-toxic organic or inorganic base addition salt of the compounds of SEQ ID NO:1 or SEQ ID NO: 2, and/or any other variants and/or fragments of oxytocin as described herein. Examples of illustrative inorganic bases that form suitable salts are alkali and earth alkali metal hydroxides and carbonates such as sodium hydroxide, sodium carbonate, potassium hydroxide, potassium carbonate, calcium hydroxide, calcium carbonate, magnesium hydroxide, magnesium carbonate and ammonia. Examples of illustrative organic bases that form suitable salts are methylamine, dimethylamine, trimethylamine and picoline. Either mono- or dibasic salts could be formed with such compounds. The base addition salts of these compounds are generally water soluble and different hydrophilic organic solvents and, that compared to the free base forms thereof, generally display higher melting points.

The non-ionic cellulose ethers of the pharmaceutical composition of the present invention are based on cellulose, which has been chemically modified in order to attain solubility in water by substitution of various groups onto the cellulose backbone. The substituents are characterised to have no electric charge when dissolved in water at a neutral pH.

The properties of the non-ionic cellulose ethers are determined by the molecular weight, (e.g. the degree of polymerisation), the type of substituents and also by the number and distribution of the substituents along the molecule. Hence, depending on the oxytocin and/or fragment and/or variant thereof which is present in the pharmaceutical composition, the non-ionic cellulose ether can have varying properties and will be determined according to the prevailing circumstances.

The cellulose ethers according to the present invention are non-ionic, wherein alkyl and/or hydroxyalkyl groups are attached to the anhydroglucose units by ether linkages, which form hydroxyalkylalkylcelluloses, wherein the alkyl groups have from 1 to 4 carbon atoms. Representative cellulose ethers for use in the pharmaceutical compositions according to the present invention are methyl cellulose (MC), hydroxyethylmethyl cellulose (HEMC), hydroxypropylmethylcellulose (HPMC), hydroxyethylethylcellulose (HEEC), and hydroxypropylcellulose (HPC). These polymers have substituents that are either nonpolar (e.g. methyl) or slightly polar (e.g. hydroxyethyl), which in combination with the hydrophilic cellulose backbone provide an amphiphilic polymer.

Accordingly, the present invention relates to pharmaceutical compositions wherein the at least one non-ionic cellulose ether is selected from one or more of the following cellulose ethers: MC, HPMC, HEEC, HEMC and/or HPC, or as further exemplified herein. In one aspect of a pharmaceutical composition according to the present invention, said non-ionic cellulose ether is hydroxypropylmethylcellulose (HPMC).

The pH of a pharmaceutical composition according to the present invention, and applicable to all embodiments and aspects thereof as defined herein can be in the range of between about 3 and 4.5, such as between about 3.5 and about 4.5, between about 3.5 and 4, between about 3 and 4, between about 3 and 3.5, between about 3 and 3.1, between about 3 and 3.2, between about 3 and 3.3, between about 3 and 3.4, between about 3 and 3.6, between about 3 and 3.7, between about 3 and 3.8, between about 3 and 3.9, between about 3.1 and 3.2, between about 3.1 and 3.3, between about 3.1 and 3.4, between about 3.1 and 3.5, between about 3.1 and 3.6, between about 3.1 and 3.7, between about 3.1 and 3.8, between about 3.1 and 3.9, between about 3.2 and 3.3, between about 3.2 and 3.4, between about 3.2 and 3.5, between about 3.2 and 3.6, between about 3.2 and 3.7, between about 3.2 and 3.8, between about 3.2 and 3.9, between about 3.3 and 3.5, between about 3.3 and 3.6, between about 3.3 and 3.7, between about 3.3 and 3.8, or between about 3.3 and 4. It should be noted that these values are not exact, meaning that they can vary slightly around the values provided.

The pH of a pharmaceutical composition as defined herein can be regulated by adding a pH regulating agent to said pharmaceutical composition, such as a buffer. In the context of the present invention, said buffer can be a lactate buffer, a citrate buffer, a phosphate buffer, or a mixture thereof, but is not limited thereto.

The concentration of a buffer to be added to the pharmaceutical composition according to the invention can be between about 20 and 100 mM, such as between about 25 mM and 100 mM, or about 25 to 50 mM, about 25 mM to 75 mM, or about 50 to 70 mM in an aqueous solution, but is not limited thereto. It should be noted that these values are not exact, meaning that they can vary slightly around the values provided. Depending on which pH is required and which buffer is used in the pharmaceutical composition according to the present invention, the concentration of the buffer will vary in accordance with the above.

In one aspect of the present invention, a pharmaceutical composition comprises oxytocin (SEQ ID NO:1) and hydroxypropylmethylcellulose (HPMC), optionally in combination with buffers, other pH regulating agents or additional components as exemplified herein, such as a preservative, such as benzoic acid. In one aspect, the pH of said composition of oxytocin and HPMC is within the range of between about 3-4, such as about 3-3.5, about 3.1 to 3.6, or about 3 to 3.8, or as further defined herein.

In a pharmaceutical composition according to the present invention, the concentration of oxytocin and/or a fragment and/or a variant thereof as defined herein can be between about 0.1 to 1.5 mg/g, such as about 0.5 to about 1.5 mg/g, about 0.5 to about 1 mg/g, about 0.5 to about 1.2 mg/g, about 0.2 to about 0.5 mg/g, about 0.1 to about 0.8 mg/g, or about 0.2 to about 1.2 mg/g of the total pharmaceutical composition as defined herein.

Herein, mg/g can be considered approximately equivalent to mg/ml, in view of the pharmaceutical composition that is being used. Accordingly, the concentration of oxytocin and/or a fragment and/or a variant thereof as defined herein can be between about 0.1 to 1.5 mg/ml, such as about 0.5 to about 1.5 mg/ml, about 0.5 to about 1 mg/ml, about 0.5 to about 1.2 mg/ml, about 0.2 to about 0.5 mg/ml, about 0.1 to about 0.8 mg/ml, or about 0.2 to about 1.2 mg/ml of the total pharmaceutical composition as defined herein. Hence, this means that 1 ml of the total pharmaceutical composition may contain between about 0.1 to 1.5 mg/ml of oxytocin.

In one aspect, a pharmaceutical composition according to the present invention comprises about: 1 mg/g oxytocin, about 2 wt % hydroxypropylmethylcellulose in about 25 mM citrate or lactate buffer, and optionally about 1 mg/g benzoic acid.

In another aspect, a pharmaceutical composition according to the present invention comprises about 0.9 mg/g oxytocin, about 1.1 mg/g benzoic acid, and about 2 wt % hydroxypropylmethylcellulose (HPMC) in about 25 mM lactate buffer.

The pH of the pharmaceutical compositions described in the above are within the range of between about 3 and 4, such as about 3 to about 3.5 or about 3.1 to about 3.6 or about 3.2 to about 3.5, or as further exemplified herein.

The concentration of the at least one non-ionic cellulose ether, such as hydroxypropylmethylcellulose (HPMC) is provided in relation to the pH regulating agent of the pharmaceutical composition, such as a buffer, as presented herein, e.g. 2 wt % or 3 wt % non-ionic cellulose ether in 25 mM buffer provides a certain viscosity due to the amount of the at least one non-ionic cellulose ether present in said buffer. Accordingly, the concentration of the non-ionic cellulose ether is presented in weight % (wt %) in said buffer, or other pH regulating agent. In the total pharmaceutical composition, the amount of non-ionic cellulose ether is somewhat less due to the addition of the therapeutic substance (oxytocin and/or one or more fragment(s) and/or variant(s) thereof as disclosed herein) to said composition.

The concentration of oxytocin and/or one or more fragment(s) and/or variant(s) thereof as defined herein is provided in relation to the total pharmaceutical composition, i.e. the buffer and the non-ionic cellulose ether, and optionally other additives such as a preservative. Hence, 1 mg/g oxytocin means that 1 mg oxytocin is present in 1 g of total pharmaceutical composition. In addition, as previously mentioned herein, 1 mg/ml means that 1 mg of oxytocin is present in 1 ml of total pharmaceutical composition In the context of the present invention, a dosage form of oxytocin, and/or one or more fragment(s) and/or variant(s) thereof administered to a subject in need thereof may comprise between about 50 and 600 IU of oxytocin and/or one or more fragment(s) and/or variant(s) thereof as defined herein, such as about 100, 200, 250, 300, 350 or 400 IU. One international unit (IU) of oxytocin is the equivalent of about 1.67 micrograms of pure peptide. Accordingly, a composition of 1 g of oxytocin gel, 400 IU, is equivalent to about 0.67 mg/g (Ph Eur).

The present invention also relates to the pharmaceutical compositions as disclosed herein for use as medicaments. In one aspect of the present invention, the invention relates to a pharmaceutical composition comprising oxytocin (SEQ ID NO:1), and/or one or more fragment(s) and/or variant(s) thereof according to SEQ ID NO:2, as well as pharmaceutically acceptable salts thereof and hydroxypropylmethylcellulose (HPMC), optionally in combination with buffers, other pH regulating agents and/or additional components as exemplified herein, such as a preservative such as benzoic acid, for use as a medicament. Such a pharmaceutical composition has a pH within the ranges as exemplified herein. An example of a medical use of the compositions of the present invention is for vaginal use, such as vaginal atrophy. Such a medical use of oxytocin is shown by the present inventors in WO0178758.

For examples of other medical uses of oxytocin which the pharmaceutical compositions according to the present invention are useful we refer to WO02102832, WO02067974, WO03017922, WO0018424, WO9843661, WO9843662, and WO9843660. Hence, the present invention also relates to a pharmaceutical composition as presented herein for a medical use as exemplified in any of the above patent documents. Such medical uses are e.g. to create eustasis, cancer in situ and cervicitis, inflammation, cell regeneration, wound healing, preference and create acceptance, and for the treatment of pain, when a pharmaceutical composition according to the present invention meaning is suitable to use in the treatment of such a disease state, such as when a topical treatment is suitable for the treatment thereof.

By the expression "eustasis" it is referred to a psychophysiological state, i.e. a combination of a psychological and physiological state. The psychological state is characterized by calm and positive social interactions such as trust, for example during breast-feeding. The physiological state is characterized by muscle relaxation, lowered cardiovascular activity and enhanced gastrointestinal activity. Besides, pulse rate and blood pressure are kept at a low, healthy and balanced level, and the vagally controlled gastrointestinal tract is activated, promoting digestion and storage of nutrients.

By the expression "cancer in situ and cervicitis" it is referred to consequences of diseases in vagina and cervix originating from infections, as well as inflammations. In the context of the invention, cancer in situ is related to the cervix. Such diseases include, besides cancer in situ and cervicitis, also precancerous disease states, squamous cell carcinoma, and koilocytosis. By cancer in situ is meant a neoplastic entity wherein the tumour cells are confined to the epithelium of origin, without invasion of the basement membrane. By cervicitis is meant inflammation of the cervix uteri i.e. the lower and narrow end of the uterus, between the isthmus and the ostium uteri. The epithelium of the cervix uteri is quite different from the epithelium of the rest of the uterus. Koilocytosis is a consequence of herpes virus.

The pharmaceutical compositions as defined herein are all encompassed for topical use, such as for vaginal use. When for vaginal use, this could be for the treatment of a climacteric disorder, such as vaginal atrophy or any other disorders mentioned in WO0178758. Hence, in one aspect the present invention relates to a pharmaceutical composition comprising oxytocin (SEQ ID NO:1), and/or one or more fragment(s) and/or variant(s) thereof according to SEQ ID NO:2, as well as pharmaceutically acceptable salts thereof and hydroxypropylmethylcellulose (HPMC), optionally in combination with buffers, other pH regulating agents or additional components as exemplified herein, such as benzoic acid for vaginal use, such as for the treatment of a climacteric disorder, e.g. vaginal atrophy. The pH of such a pharmaceutical composition can be within the range of about 3 to about 4, such as about 3 to about 3.5, about 3.1 to about 3.6 or about 3.1 to about 3.8, or as otherwise exemplified herein.

In all aspects of the present invention, it is to be understood that whenever it is referred to a certain medical use of said pharmaceutical composition, such as in the use in treating vaginal atrophy, this also refers to the use of oxytocin and/or one or more fragment(s) and/or variant(s) thereof, as defined herein, and at least one non-ionic cellulose ether in the manufacture of a medicament for the treatment of the certain disease, such as exemplified herein, wherein said medicament has a pH within the range of between about 3 and 4, such as about 3 and 3.5, or as further exemplified herein.

As shown herein, the presence of at least one non-ionic cellulose ether in the pharmaceutical composition effectively improves the stability of the oxytocin molecule therein. Hence, the present invention also relates to the use of at least one non-ionic cellulose ether for stabilizing, alternatively improving the stability of a pharmaceutical composition comprising oxytocin (SEQ ID NO:1) and/or one or more fragment(s) and/or variant(s) of oxytocin, as defined in SEQ ID NO:2 or as otherwise defined herein. In one aspect, the invention relates to the use of the at least one non-ionic cellulose ether hydroxypropylmethylcellulose (HPMC) for stabilizing, alternatively improving the stability a pharmaceutical composition comprising oxytocin (SEQ ID NO:1) and/or a fragment and/or a variant of oxytocin, as well as pharmaceutically acceptable salts thereof as defined in SEQ ID NO:2, or as otherwise defined herein, said pharmaceutical composition optionally in addition comprising a buffer, other pH regulating agents or additional components as exemplified herein, such as a preservative. As previously mentioned herein, the combination of using a low pH in the pharmaceutical composition further improves the stabilizing effect of the at least one non-ionic cellulose ether. Without being bound by a specific theory, the at least one non-ionic cellulose ether appears to stabilize the oxytocin molecule and/or one or more fragment(s) and/or variant(s) thereof as defined herein by making it less prone to degradation and/or aggregation or other structural changes, potentially by not interfering with the oxytocin molecule.

Whenever it is referred to an improved stability/stabilizing effect herein, this may mean the reduction of aggregation and/or degradation or other structural changes of the oxytocin molecule in the pharmaceutical composition defined herein, but is not bound to this specific theory. In accordance with such a theory, a reduction in aggregation and/or degradation or other structural changes is accompanied by an improved stability of the oxytocin molecule. The improvement in stability by a pharmaceutical composition comprising at least one non-ionic cellulose ether is further illustrated in the experimental section comprising comparative examples with the gel CMC.

In another aspect, the present invention relates to a method for preparing a pharmaceutical composition with improved stability comprising the steps of:
a) preparing a buffer solution and adjusting the pH thereof,
b) adding oxytocin (SEQ ID NO: 1) and/or one or more fragment(s) and/or variant(s) thereof in accordance with SEQ ID NO:2 or as otherwise defined herein, as well as pharmaceutically acceptable salts thereof to said buffer, and
c) adding at least one non-ionic cellulose ether to the solution obtained in step b);
wherein optionally a preservative, such as benzoic acid, is added to the buffer solution of step a) before said oxytocin (SEQ ID NO:1) and/or one or more fragment(s) and/or variant(s) thereof in accordance with SEQ ID NO:2 or as otherwise defined herein is/are added to said buffer solution and wherein the pH of said pharmaceutical composition is regulated to fall within the range of between about 3 and about 4, such as within the range of about 3 and about 3.5, or as otherwise exemplified herein. After step c) the solution is left for a while to obtain a viscous solution or a gel. Typically, said viscous solution or gel is obtained after about 1-2 days. Said method also in some aspects encompasses the use of other pH regulating agents than buffers, such as organic and inorganic acids and bases, such as acetic acid, citric acid, phosphoric acid and hydrochloric acid and sodium hydroxide, which would hence be used in step a) of said method.

In the present method, what is intended is that it is the stability of oxytocin, and/or one or more fragment(s) and/or variant(s) thereof as disclosed herein that is improved by preparing the composition together with the at least one non-ionic cellulose ether. In one aspect of the present method, said at least one non-ionic cellulose ether is hydroxypropylmethylcellulose (HPMC). In one aspect, the method relates to preparing a pharmaceutical composition comprising oxytocin (SEQ ID NO:1) and hydroxypropylmethylcellulose (HPMC).

Administration of an oxytocin molecule may in certain aspects be facilitated by applying touch, pressure, massage, heat, or infrared light on the skin, which leads to enhanced skin permeability. Hirvonen, J., Kalia, Y N, and Gay, R H. Transdermal delivery of peptides by iontophoresis. Nat Biotechnol December 1996; 14(13): 1710-1713 describes how to enhance the transport of a drug via the skin using the driving force of an applied electric field. Iontophoresis may be effected at a slightly basic pH.

There are different processes described for the synthetic production of oxytocin; commercial processes are for instance described in U.S. Pat. Nos. 2,938,991 and 3,076,797.

In one aspect, the present invention relates to a pharmaceutical composition comprising a. oxytocin (SEQ ID NO:1), and/or one or more fragment(s) and/or variant(s) thereof according to SEQ ID NO:2, as well as pharmaceutically acceptable salts thereof; and b. at least one non-ionic cellulose ether;

wherein SEQ ID NO:2 is $X_1$—$X_2$—$X_3$—$X_4$-Asn-Cys-$X_5$—$X_6$—$X_7$—$X_8$—$NH_2$ wherein $X_1$ is selected from the group consisting of Cys and nothing;

$X_2$ is selected from the group consisting of Tyr, Phe, and nothing;

$X_3$ is selected from the group consisting of Ile, Val, Hoph, Phe, Cha, and nothing;

$X_4$ is selected from the group consisting of Gln, Ser, Thr, Cit, Arg, and Daba;

$X_5$ is selected from the group consisting of Pro and nothing;

$X_6$ is selected from the group consisting of Ile, Leu, nothing, Val, Hos, Daba, Thr, Arg, and Cit;

$X_7$ is selected from the group consisting of Gly, nothing, and Ala;

$X_8$ is selected from the group consisting of Gly and nothing;

wherein oxytocin, and/or said one or more fragment(s) and/or variant(s) thereof is/are present in an amount of about 0.1 to 1.5 mg/g, such as 0.5 to about 1.5 mg/g, about 0.5 to about 1 mg/g, about 0.5 to about 1.2 mg/g, about 0.2 to about 0.5 mg/g, about 0.1 to about 0.8 mg/g, or about 0.2 to about 1.2 mg/g of the total composition, and wherein said at least one non-ionic cellulose ether is present in an amount of about 1-3 wt %, such as about 2 wt % or 3 wt % in a pH regulating agent, such as a buffer, said buffer having a concentration of about 25 mM to about 100 mM. In one aspect, said at least one non-ionic cellulose ether is hydroxypropyl methylcellulose.

In some aspects, the pharmaceutical compositions according to the present invention can optionally comprise other components, such as inert components or components having a physical or biological function. In some aspects, an antibiotic or an analgesic is additionally present in a pharmaceutical composition according to the invention.

The invention also relates to a method for treating a climacteric disorder, such as vaginal atrophy, in a patient in need thereof comprising administering a suitable amount of a pharmaceutical composition comprising a. oxytocin (SEQ ID NO:1), and/or one or more fragment(s) and/or variant(s) thereof according to SEQ ID NO:2, as well as pharmaceutically acceptable salts thereof; and b. at least one non-ionic cellulose ether;

to a patient in need thereof, wherein the pH of said pharmaceutical composition is within the range of between about 3 and 4, or as otherwise exemplified herein. Said pharmaceutical composition for use in a method for treating a climacteric disorder can be any pharmaceutical composition as disclosed herein. In one aspect said pharmaceutical composition which is administered to a patient in need thereof comprises oxytocin and hydroxypropylmethylcellulose (HPMC).

The present invention also relates to a method for treating any disorder as previously mentioned herein comprising administering a suitable amount of a pharmaceutical composition comprising a. oxytocin (SEQ ID NO:1), and/or one or more fragment(s) and/or variant(s) thereof according to SEQ ID NO:2, as well as pharmaceutically acceptable salts thereof; and b. at least one non-ionic cellulose ether;

to a patient in need thereof, wherein the pH of said pharmaceutical composition is within the range of between about 3 and 4, or as otherwise exemplified herein. Said pharmaceutical composition for use in a method for treating for treating any disorder as previously mentioned herein can be any pharmaceutical composition as disclosed herein. In one aspect said pharmaceutical composition which is administered to a patient in need thereof comprises oxytocin and hydroxypropylmethylcellulose (HPMC).

In another aspect, the present invention relates to a pharmaceutical composition comprising about 1 mg/g oxytocin, about 2 wt % hydroxypropylmethylcellulose (HPMC) in about 25 mM citrate or lactate buffer and optionally about 1 mg/g benzoic acid and wherein the pH of said composition is about 3.

In another aspect, the present invention relates to a pharmaceutical composition comprising about 1 mg/g oxytocin, about 2 wt % hydroxypropylmethylcellulose (HPMC) in about 25 mM lactate buffer and wherein the pH of said composition is about 3.8.

In another aspect, the present invention relates to a pharmaceutical composition comprising about 0.9 mg/g oxytocin, about 1.1 mg/g benzoic acid, about 2 wt % hydroxypropylmethylcellulose (HPMC) in about 25 mM lactate buffer and wherein the pH of said composition is about pH 3.8.

In another aspect, the present invention relates to a pharmaceutical composition comprising oxytocin, hydroxypropylmethylcellulose, a citrate or a lactate buffer, and optionally benzoic acid. In one aspect, said pharmaceutical composition comprises about: 1 mg/g oxytocin, about 2 wt % hydroxypropylmethylcellulose in about 25 mM citrate or lactate buffer, and optionally about 1 mg/g benzoic acid.

In another aspect, the present invention relates to a pharmaceutical composition comprising about: 1 mg/g oxytocin, 2 wt % hydroxypropylmethylcellulose in a 25 mM lactate buffer, and optionally 1 mg/g benzoic acid.

In another aspect, the present invention relates to a pharmaceutical composition comprising about: 0.8 mg/g oxytocin, 3 wt % hydroxypropylmethylcellulose in a 22 mM lactate buffer, and optionally 1 mg/g benzoic acid.

In another aspect, the present invention relates to a pharmaceutical composition comprising about: 0.4 mg/g oxytocin, 3 wt % hydroxypropylmethylcellulose in a 22 mM lactate buffer, and optionally 1 mg/g benzoic acid.

In another aspect, the present invention relates to a pharmaceutical composition comprising about: 0.2 mg/g oxytocin, 3 wt % hydroxypropylmethylcellulose in a 22 mM lactate buffer, and optionally 1 mg/g benzoic acid.

As previously mentioned herein, a dosage form of a pharmaceutical composition comprising oxytocin (SEQ ID NO:1), and/or one or more fragment(s) and/or variant(s) thereof as defined herein, may comprise between about 50 and 600 IU of oxytocin and/or one or more fragment(s) and/or variant(s) thereof as defined herein, such as about 100, 200, 250, 300, 350 or 400 IU.

The present invention also relates to a kit comprising a pharmaceutical composition comprising
  a. oxytocin (SEQ ID NO:1), and/or one or more fragment(s) and/or variant(s) thereof according to SEQ ID NO:2, as well as pharmaceutically acceptable salts thereof; and
  b. at least one non-ionic cellulose ether;
and a dispenser for dispensing said pharmaceutical composition optionally in combination with instructions for use of said pharmaceutical composition, wherein the pH of said pharmaceutical composition is within the range of between about 3 and 4, or as otherwise exemplified herein. In a kit as presented herein, any pharmaceutical composition as disclosed herein can be used. Said dispenser present in said kit may e.g. be in the form of a plastic tube. The kit may also comprise one or more containers each comprising one or more of a pharmaceutically acceptable carrier, adjuvant and/or excipient.

The pharmaceutical composition disclosed herein may e.g. be an aqueous composition comprising the oxytocin and the non-ionic cellulose ether.

The present invention is illustrated in the following experimental section, but is not intended to be limited thereto.

Experimental Section

Stressed Stability Studies of Oxytocin in Citrate/Lactate Buffers with Na-CMC/HPMC at 70° C.

Summary

The stability of oxytocin in citrate buffer with or without benzoic acid and with or without Na-CMC was studied at 70° C. for two weeks.

In another set of samples the stability of oxytocin in citrate buffer with or without benzoic acid and with or without HPMC (Hypromellose or hydroxylpropylmethylcellulose) studied at 70° C. for three weeks.

In a third set of samples the stability of oxytocin in lactate buffer with HPMC and with or without benzoic acid was studied at 70° C. for two weeks.

Background

The stability of oxytocin in aqueous solutions of different pH has been studied earlier[1]. In this study it was concluded that best stability was obtained at pH 4.5. In a recent stability study[2] it was shown that the stability of oxytocin is highly dependent on formulation and storage conditions.

In a third study the stability of oxytocin in lactate buffer and citrate buffer respectively was studied with benzoic acid as a preservative instead of the parabens used in previous studies[3]. Parabens may cause degradation of the gelling agent Na-CMC[4]. However, decreased viscosity was observed with benzoic acid as well.

In the present study the effect of the gelling agent (Na-CMC/HPMC) is studied in citrate/lactate buffer and with or without benzoic acid as preservative.

Equipment

HPLC-system according to Ph. Eur. 2.2.29
HPLC system: Alliance 2695 from Waters, UV detection at 220 nm
Column: YMC.-PAC ODS-A C18 250*4.6 mm, 5 μm
Mobile phase: A: 15.6 g/l Sodium dihydrogen phosphate
B: Acetonitrile:Water (50:50)
Chromatography software: MassLynx version 4.1 from Waters
pH meter: Jenway 370
Chemicals
Acetonitrile HPLC grade S (ACN), Rathburn chemicals
Sterilized water, Baxter
Sodium dihydrogen phosphate, Merck, 6346
Oxytocin was obtained from Grindeks, Riga, Latvia Sample Preparation The buffer solution was prepared by dissolving the appropriate amount of either citric acid or lactic acid in distilled water, about 90% of the total volume. The pH was adjusted to the desired value by the drop-wise addition of 5 M NaOH (aq.) during magnetic stirring. Finally, the solution was transferred to a volumetric flask and the volume was adjusted to the final volume by distilled water.

The preservative benzoic acid was weighed in a glass flask and the required volume of buffer solution was added. After sealing the flask, benzoic acid was dissolved by treatment of the flask in a warm (about 50° C.) ultrasonication bath for about 30 min. After cooling to room temperature oxytocin was added to the clear solution and dissolved by gentle mixing. Finally, the required amount of non-ionic cellulose ether was added and the mixture was shaken by hand then left to swell and dissolve at room temperature to give a viscous solution/gel.

The final samples were stored in glass vials with butyl rubber stoppers and Al crimp seals.

| Sample | Composition |
|---|---|
| ACA101108-1 | 1.0 mg/g oxytocin in 100 mM citrate buffer, pH 3.1 |
| ACA101108-2 | 1.2 mg/g oxytocin + 1.0 mg/g benzoic acid in 100 mM citrate buffer, pH 3.1 |
| ACA101108-3 | 1.0 mg/g oxytocin + 1.0 mg/g benzoic acid + 2.6% Na-CMC in 100 mM citrate buffer, pH 3.1 |
| ACA101108-4 | 1.0 mg/g oxytocin + 2.6% Na-CMC in 100 mM citrate buffer, pH 3.1 |
| ACA101123-1 | 1.0 mg/g oxytocin in 25 mM citrate buffer, pH 3.10 |
| ACA101123-2 | 1.0 mg/g oxytocin + 1.0 mg/g benzoic acid in 25 mM citrate buffer, pH 3.10 |
| ACA101123-3 | 1.0 mg/g oxytocin + 1.0 mg/g benzoic acid + 2.0% HPMC in 25 mM citrate buffer, pH 3.10 |
| ACA101123-4 | 1.0 mg/g oxytocin + 2.0% HPMC in 25 mM citrate buffer, pH 3.10 |
| ACA101207-1 | 1.0 mg/g oxytocin + 2.0% HPMC in 25 mM lactate buffer, pH 3.79 |
| ACA101207-2 | 0.9 mg/g oxytocin + 1.1 mg/g benzoic acid + 2.0% HPMC in 25 mM lactate buffer, pH 3.79 |

Experimental Procedure

The samples were stored at different temperatures and samples were withdrawn for analysis according to the stability scheme below. Before analysis, 30 mg of each of the liquid samples was diluted with 1.00 ml of mobile phase A and then injected into the HPLC-system.

Analysis

All samples were visually inspected and their pH-values were measured prior to analysis.

HPLC

Mobile Phase:
A: 15.6 g/l Sodium dihydrogen phosphate
B: Acetonitrile:Water (50:50)

Gradient Profile Parameters:

| Time (min) | A (%) | B (%) |
|---|---|---|
| 0 | 95.0 | 5.0 |
| 1 | 95.0 | 5.0 |
| 30.0 | 5.0 | 95.0 |
| 40.0 | 5.0 | 95.0 |
| 45.0 | 95.0 | 5.0 |

Flow: 1.00 ml
Injection volume: 20 μl
Injector wash solution: Water:Acetonitrile Evaluation All samples were first visually inspected and analysed changes in colour or tendencies for precipitation and changes in viscosity. Then pH was measured and the samples were further analysed for content of oxytocin and benzoic acid. Concentrations were determined against external standard curves for oxytocin and benzoic acid, respectively. All samples were prepared in duplicates and subsequently analysed by a single HPLC-injection (EXP-11-AJ1634).

Results

TABLE 1 a)-c) pH, oxytocin and benzoic acid content of the samples of the series ACA101108 after up to 2 weeks of storage.

Table 1a)

| | | Time 0 | | | |
|---|---|---|---|---|---|
| | | Benzoic acid | | Oxytocin | |
| Sample | pH | mg/g | % | mg/g | % |
| ACA101108-1 | 3.15 | x | x | 0.93 | 100 |
| ACA101108-2 | 3.12 | 1.30 | 108 | 1.18 | 100 |
| ACA101108-3 | 3.73 | 1.27 | 127 | 0.96 | 100 |
| ACA101108-4 | 3.8 | x | x | 0.93 | 100 |

Table 1b)

| | | 1 week 70° | | | |
|---|---|---|---|---|---|
| | | Benzoic acid | | Oxytocin | |
| Sample | pH | mg/g | % | mg/g | % |
| ACA101108-1 | 3.10 | x | x | 0.36 | 38.7 |
| ACA101108-2 | 3.07 | 1.11 | 93 | 0.47 | 39.8 |
| ACA101108-3 | 3.81 | 1.07 | 107 | 0.23 | 24 |
| ACA101108-4 | 3.82 | x | x | 0.24 | 25.8 |

Table 1c)

| | | 2 weeks 70° | | | |
|---|---|---|---|---|---|
| | | Benzoic acid | | Oxytocin | |
| Sample | pH | mg/g | % | mg/g | % |
| ACA101108-1 | ND | x | x | 0.29 | 31.1 |
| ACA101108-2 | ND | 1.12 | 112 | 0.34 | 28.8 |
| ACA101108-3 | ND | 1.13 | 113 | 0.15 | 15.6 |
| ACA101108-4 | ND | x | x | 0.20 | 21.5 |

ND = not determined.

TABLE 2 a)-d) pH, oxytocin and benzoic acid content of the samples of the series ACA101123 after up to 3 weeks of storage.

Table 2a)

| | | Time 0 | | | |
|---|---|---|---|---|---|
| | | Benzoic acid | | Oxytocin | |
| Sample | pH | mg/g | % | mg/g | % |
| ACA101123-1 | 3.25 | x | x | 0.98 | 100 |
| ACA101123-2 | 3.22 | 0.95 | 95 | 0.94 | 100 |
| ACA101123-3 | 3.25 | 0.87 | 87 | 0.88 | 100 |
| ACA101123-4 | 3.31 | x | x | 0.86 | 100 |

Table 2b)

| | | 1 week 70° | | | |
|---|---|---|---|---|---|
| | | Benzoic acid | | Oxytocin | |
| Sample | pH | mg/g | % | mg/g | % |
| ACA101123-1 | ND | x | x | 0.75 | 76.5 |
| ACA101123-2 | ND | 1.20 | 120 | 0.77 | 81.9 |
| ACA101123-3 | ND | 1.12 | 112 | 0.74 | 84.1 |
| ACA101123-4 | ND | x | x | 0.78 | 90.7 |

Table 2c)

| | | 2 weeks 70° | | | |
|---|---|---|---|---|---|
| | | Benzoic acid | | Oxytocin | |
| Sample | pH | mg/g | % | mg/g | % |
| ACA101123-1 | 3.31 | x | x | 0.52 | 53.1 |
| ACA101123-2 | 3.29 | 1.04 | 109 | 0.52 | 55.3 |
| ACA101123-3 | 3.25 | 0.98 | 112 | 0.50 | 56.8 |
| ACA101123-4 | 3.32 | x | x | 0.50 | 58.1 |

Table 2d)

| | | 3 weeks 70° | | | |
|---|---|---|---|---|---|
| | | Benzoic acid | | Oxytocin | |
| Sample | pH | mg/g | % | mg/g | % |
| ACA101123-1 | 3.30 | x | x | 0.46 | 46.9 |
| ACA101123-2 | 3.25 | 1.18 | 124 | 0.51 | 54.3 |

TABLE 2-continued a)-d) pH, oxytocin and benzoic acid content of the samples of the series ACA101123 after up to 3 weeks of storage.

| ACA101123-3 | 3.31 | 0.82 | 94.3 | 0.43 | 48.9 |
| ACA101123-4 | 3.33 | x | x | 0.47 | 54.7 |

TABLE 3 a)-c) pH, oxytocin and benzoic acid content of the samples of the series ACA101207 after up to 2 weeks of storage.

Table 3a)

Time 0

| | | Benzoic acid | | Oxytocin | |
|---|---|---|---|---|---|
| Sample | pH | mg/g | % | mg/g | % |
| ACA101207-1 | 4.17 | x | x | 0.98 | 100 |
| ACA101207-2 | 3.88 | 1.06 | 100 | 0.95 | 100 |

Table 3b)

1 week 70°

| | | Benzoic acid | | Oxytocin | |
|---|---|---|---|---|---|
| Sample | pH | mg/g | % | mg/g | % |
| ACA101207-1 | 3.98 | x | x | 0.58 | 59.2 |
| ACA101207-2 | 3.78 | 1.00 | 94.3 | 0.58 | 61.1 |

Table 3c)

2 weeks 70°

| | | Benzoic acid | | Oxytocin | |
|---|---|---|---|---|---|
| Sample | pH | mg/g | % | mg/g | % |
| ACA101207-1 | 3.75 | x | x | 0.50 | 51.0 |
| ACA101207-2 | 3.67 | 1.06 | 100.00 | 0.51 | 53.7 |

TABLE 4

Appearance and viscosity of the samples after up to 3 weeks of storage.

| Storage Temperature | Time | ACA101108-1 Appearance | Viscosity | ACA101108-2 Appearance | Viscosity |
|---|---|---|---|---|---|
| 70° C. | 2 weeks | Clear | NA | Clear | NA |

| Storage Temperature | Time | ACA101108-3 Appearance | Viscosity | ACA101108-4 Appearance | Viscosity |
|---|---|---|---|---|---|
| 70° C. | 2 weeks | Slightly yellow | Very low visc | Clear | Very low visc |

| Storage Temperature | Time | ACA101123-1 Appearance | Viscosity | ACA101123-2 Appearance | Viscosity |
|---|---|---|---|---|---|
| 70° C. | 3 weeks | Clear | NA | Clear | NA |

| Storage Temperature | Time | ACA101123-3 Appearance | Viscosity | ACA101123-4 Appearance | Viscosity |
|---|---|---|---|---|---|
| 70° C. | 3 weeks | Slightly yellow | Very low visc | Very slightly yellow | Very low visc |

| Storage Temperature | Time | ACA101207-1 Appearance | Viscosity | ACA101207-2 Appearance | Viscosity |
|---|---|---|---|---|---|
| 70° C. | 2 weeks | Very slightly yellow | Low visc | Slightly yellow | Low visc |

Discussion

In the earlier stability study of oxytocin, the degradation rate was investigated at different pH-values. This study showed that the degradation of oxytocin in a buffered aqueous solution of pH 3, stored at 70° C. for 7 days was about 15% (area %). The corresponding degradation at pH 4 was approximately 35% (area %). In Table 1 above, it is shown that the degradation of oxytocin is significantly more extensive under comparable pH conditions, ca 60% and 75%, respectively. These data indicate that the stability of oxytocin might be dependent not only on pH but also on the type of acid used for buffering. Furthermore, data suggests that Na-CMC in itself has a negative impact on stability.

Table 2 shows data from analysis of oxytocin solutions in which Na-CMC has been replaced by a neutral cellulose derivative, HPMC, and in which the buffer is 25 mM citrate. These data, again, show a significantly better stability of oxytocin and the corresponding degradation is in the magnitude of about 20%. Table 3 shows the corresponding degradation of oxytocin in a HPMC containing formulation in which lactate is used as buffering agent. These data indicate a similar stability for oxytocin in lactate and citrate under comparable pH conditions. Former formulations, in which lactate was used in combinations with Na-CMC, resulted in precipitation and haziness in the formulations. This is not seen in formulations where HPMC is used together with lactate, Table 4.

From Table 4 it can be concluded that formulations with benzoic acid are slightly more yellowish than the formulations without this preservative. The formulations based on lactate are slightly more viscous than the citrate based formulations after storage at 70° C.

The above presented studies also indicate that benzoic acid is compatible with oxytocin and the ingredients used.

CONCLUSIONS

This study shows that the stability of oxytocin in an acidic environment essentially follows the pattern seen before, i.e. a better stability is seen at pH 3 than at pH 4. It is concluded that oxytocin is more stable in formulations with HPMC as the gelling agent than with Na-CMC. The viscosity of the formulations decreases upon storage at 70° C. for both gelling agents. The stability of oxytocin is similar in lactate and citrate under comparable pH conditions. Benzoic acid is concluded to be a suitable preservative.

REFERENCES

1. Hawe A. et al., *Towards heat-stable oxytocin formulations: Analysis of degradation kinetics and identification of degradation products*, Pharmaceutical Research, 2009, 26: 1679-1688.
2. *Stability study of oxytocin in aqueous solutions and dry powder*, Labagon A B, 2010.
3. Fawcett J P, et al., *Binding of parabens to sodium carboxymethylcellulose in oral liquid formulations*, Aust. J. Hosp. Pharm., 1996, 26: 552-554.
4. WO/92/09307
5. Hirvonen, J., Kalia, Y N, and Gay, R H. Transdermal delivery of peptides by iontophoresis. Nat Biotechnol December 1996; 14(13): 1710-1713

The invention claimed is:

1. A composition comprising
   a. oxytocin (SEQ ID NO:1), and/or one or more fragment(s) and/or variant(s) thereof according to SEQ ID NO:2, as well as pharmaceutically acceptable salts thereof; and
   b. at least one non-ionic cellulose ether;
   wherein SEQ ID NO:2 is
   $X_1$—$X_2$—$X_3$—$X_4$-Asn-Cys-$X_5$—$X_6$—$X_7$—$X_8$—$NH_2$
   wherein
   $X_1$ is selected from the group consisting of Cys and nothing;
   $X_2$ is selected from the group consisting of Tyr, Phe, and nothing;
   $X_3$ is selected from the group consisting of Ile, Val, Hoph, Phe, Cha, and nothing;
   $X_4$ is selected from the group consisting of Gln, Ser, Thr, Cit, Arg, and Daba;
   $X_5$ is selected from the group consisting of Pro and nothing;
   $X_6$ is selected from the group consisting of Ile, Leu, nothing, Val, Hos, Daba, Thr, Arg, and Cit;
   $X_7$ is selected from the group consisting of Gly, nothing, and Ala;
   $X_8$ is selected from the group consisting of Gly and nothing;
   further provided that SEQ ID NO: 2 is not SEQ ID NO:7;
   wherein said composition has a pH within the range of between 3 and 4.

2. A composition according to claim 1, wherein said one or more fragment(s) and/or variant(s) of oxytocin is/are selected from the group consisting of the peptides corresponding to SEQ ID NO:3-6 and 8-24.

3. A composition according to claim 1, wherein said pH is between 3 and 3.8.

4. A composition according to claim 1, wherein said pH is between 3 and 3.5.

5. A composition according to claim 1, wherein said pH is between 3 and 3.3.

6. A composition according to claim 1, further comprising a preservative.

7. A composition according to claim 1, wherein said at least one non-ionic cellulose ether is selected from the group consisting of methyl cellulose (MC), hydroxypropylmethylcellulose (HPMC), hydroxypropylcellulose (HPC), hydroxyethylethylcellulose (HEEC) and hydroxyethylmethyl cellulose (HEMC).

8. A composition according to claim 1, wherein said at least one non-ionic cellulose ether is hydroxypropylmethylcellulose (HPMC).

9. A composition according to claim 1, comprising oxytocin (SEQ ID NO:1) and hydroxypropylmethylcellulose (HPMC).

10. A composition according to claim 1, wherein the concentration of oxytocin and/or one or more fragment(s) and/or variant(s) thereof as defined in claim 1 is about 1 mg/g of said pharmaceutical composition.

11. A composition according to claim 1, said composition comprising about:
   1 mg/g oxytocin, and
   2 wt % hydroxypropylmethylcellulose in 25 mM buffer, wherein said buffer is citrate buffer or lactate buffer.

12. A composition according to claim 11, said composition further comprising about 1 mg/g benzoic acid.

13. A composition according to claim 1, further comprising a pharmaceutically acceptable carrier.

14. A composition according to claim 1, further comprising a carrier suitable for topical administration.

15. A pharmaceutical composition according to claim 1, further comprising a carrier suitable for vaginal administration.

16. A process for improving the stability of a composition comprising oxytocin (SEQ ID NO:1), and/or one or more fragment(s) and/or variant(s) thereof according to SEQ ID NO:2 as defined in claim 1, comprising adding to said composition at least one nonionic cellulose ether, wherein said composition has a pH range of between 3 and 4.

17. The process of claim 16, wherein said at least one non-ionic cellulose ether is hydroxypropylmethylcellulose (HPMC).

18. A method comprising the steps of:
a. preparing a buffer solution and adjusting the pH thereof,
b. adding oxytocin and/or one or more fragment(s) and/or variant(s) thereof as defined in claim 1, to said buffer solution, and thereafter
c. adding at least one non-ionic cellulose ether to the solution obtained in step b, wherein the pH of the resulting composition is regulated to fall between 3 and 4.

19. The Method according to claim 18, further comprising adding a preservative to the buffer solution.

20. Method according to claim 18, wherein said at least one non-ionic cellulose ether is hydroxypropylmethylcellulose (HPMC).

21. A composition comprising
a. oxytocin (SEQ ID NO:1), and/or one or more fragment(s) and/or variant(s) thereof according to SEQ ID NO:2, as well as pharmaceutically acceptable salts thereof; and
b. at least one non-ionic cellulose ether;
wherein SEQ ID NO:2 is
$X_1—X_2—X_3—X_4\text{-Asn-Cys-}X_5—X_6—X_7—X_8—NH_2$
wherein
$X_1$ is selected from the group consisting of Cys and nothing;
$X_2$ is selected from the group consisting of Tyr, Phe, and nothing;
$X_3$ is selected from the group consisting of Ile, Val, Hoph, Phe, Cha, and nothing;
$X_4$ is selected from the group consisting of Gln, Ser, Thr, Cit, Arg, and Daba;
$X_5$ is selected from the group consisting of Pro and nothing;
$X_6$ is selected from the group consisting of Ile, Leu, nothing, Val, Hos, Daba, Thr, Arg, and Cit;
$X_7$ is selected from the group consisting of Gly, nothing, and Ala;
$X_8$ is selected from the group consisting of Gly and nothing;
further provided that SEQ ID NO: 2 is not SEQ ID NO:7;
wherein said oxytocin and/or one or more fragment(s) and/or variant(s) thereof according to SEQ ID NO:2, or a pharmaceutically acceptable salt thereof is/are present in said composition in a concentration of about 0.5 to about 1.5 mg/g of the total composition, and said at least one non-ionic cellulose ether is present in an amount of about 1-3 wt %, in a pH regulating agent, said pH regulating agent having a concentration of between about 25 mM to about 100 mM, and wherein the pH of the composition is between 3 and 4.

22. A composition according to claim 21, wherein said at least one non-ionic cellulose ether is hydroxypropylmethylcellulose and is present in an amount of about 2 wt % in a buffer with a concentration of about 25 mM, said buffer being a lactate buffer or a citrate buffer.

23. A pharmaceutical composition according to claim 21, wherein said pH regulating agent is a buffer.

24. A composition according to claim 23, wherein said buffer is a lactate buffer or a citrate buffer.

25. A method for treating and/or preventing a climacteric disorder comprising administering a therapeutically effective amount of a composition according to claim 1, to a subject in need thereof.

26. A method according to claim 25, wherein said climacteric disorder is vaginal atrophy.

27. A method according to claim 25, wherein said pharmaceutical composition is administered topically to said subject in need thereof.

28. A kit comprising a composition according to claim 1 and a dispenser for said pharmaceutical composition.

29. A method according to claim 25, wherein the dose of oxytocin and/or one or more fragment(s) and/or variant(s) thereof to be administered is between about 50 and 600 IU of oxytocin and/or one or more fragment(s) and/or variant(s) thereof.

30. A method according to claim 29, wherein the dose is about 100, 200, 250, 300, 350 or 400 IU.

31. A composition according to claim 21, wherein the concentration of oxytocin in the composition is 0.1-0.8 mg/ml.

32. A composition according to claim 1, wherein the concentration of oxytocin in the composition is 0.1-0.8 mg/g.

* * * * *

UNITED STATES PATENT AND TRADEMARK OFFICE
CERTIFICATE OF CORRECTION

PATENT NO. : 9,034,821 B2  
APPLICATION NO. : 14/111072  
DATED : May 19, 2015  
INVENTOR(S) : Uvnäs-Moberg et al.

Page 1 of 1

It is certified that error appears in the above-identified patent and that said Letters Patent is hereby corrected as shown below:

In the Claims

Claim 21, Column 37, line 31, replace "lie" with "Ile".

Signed and Sealed this
Twenty-second Day of September, 2015

Michelle K. Lee
*Director of the United States Patent and Trademark Office*